United States Patent [19]

Csillag

[11] 4,015,604
[45] Apr. 5, 1977

[54] ABSORBENT PRODUCT WITH SIDE LEAKAGE CONTROL MEANS

[75] Inventor: Charles Csillag, Montreal, Canada

[73] Assignee: Personal Products Company, Milltown, N.J.

[22] Filed: Mar. 25, 1976

[21] Appl. No.: 670,509

[52] U.S. Cl. .............................. 128/287; 128/290 R
[51] Int. Cl.² .................. A41B 13/02; A61F 13/18
[58] Field of Search .......... 128/287, 290 R, 290 W, 128/290 P, 296

[56] References Cited

UNITED STATES PATENTS

| 3,071,138 | 1/1963 | Garcia | 128/290 R |
| 3,559,649 | 2/1971 | Grad | 128/290 R |
| 3,693,622 | 9/1972 | Jones, Sr. | 128/290 R |
| 3,799,167 | 3/1974 | Miller | 128/287 |
| 3,888,257 | 6/1975 | Cook | 128/296 |

FOREIGN PATENTS OR APPLICATIONS 884,608  11/1971  Canada ................ 128/290 R Primary Examiner—Aldrich F. Medbery
Attorney, Agent, or Firm—Jason Lipow

[57] ABSTRACT

An absorbent product is provided with side leakage control means. The product comprises an absorbent element having first and second major surfaces and is provided with means for retarding premature failure by side leakage, these means comprising a narrow longitudinally extending zone along each of the side edges of the product but spaced away from each of the side edges. The zone is impregnated with a hydrophobic material from major surface to major surface and the extreme longitudinal portions of the absorbent element along the longitudinal edges are free of such impregnation.

12 Claims, 10 Drawing Figures

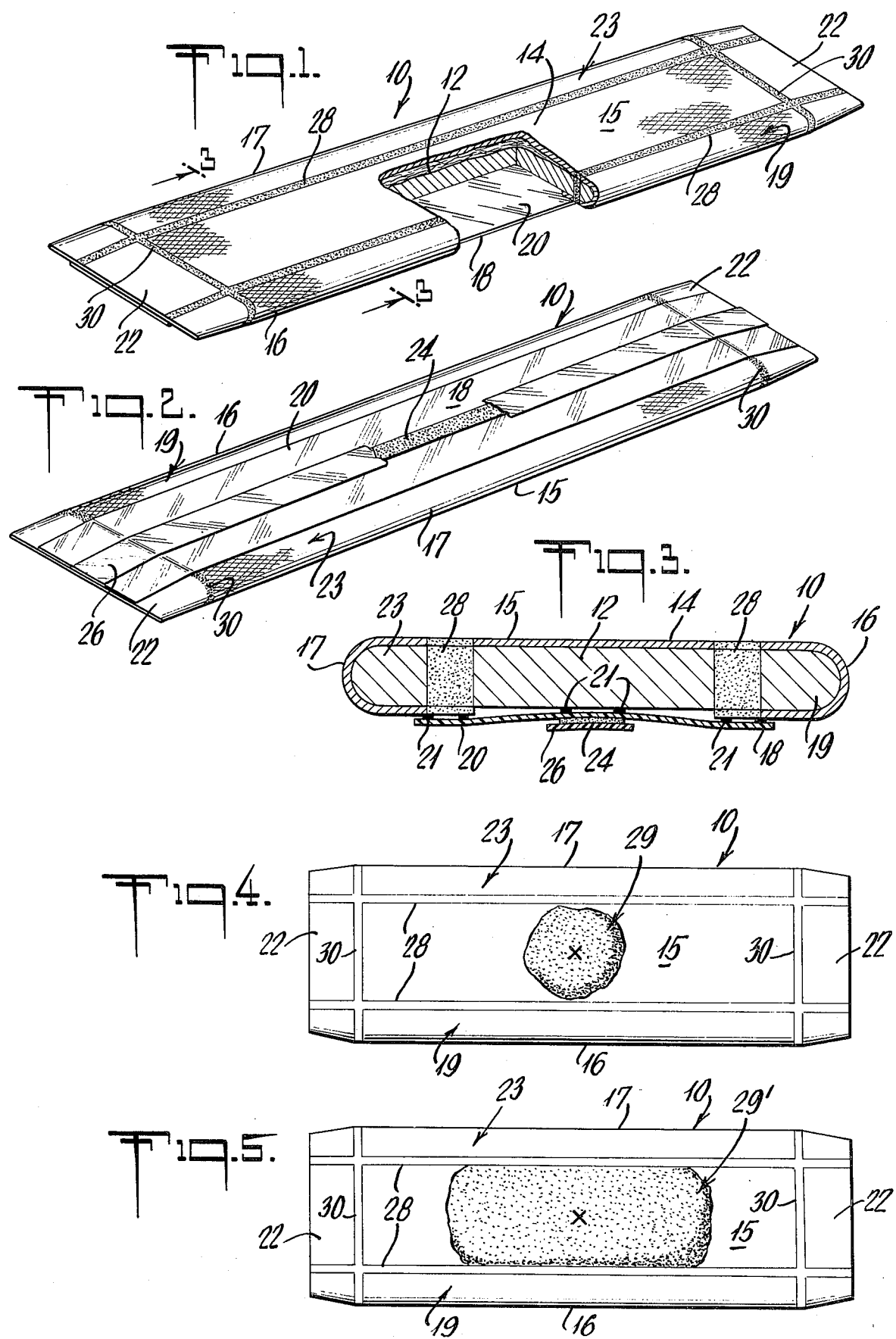

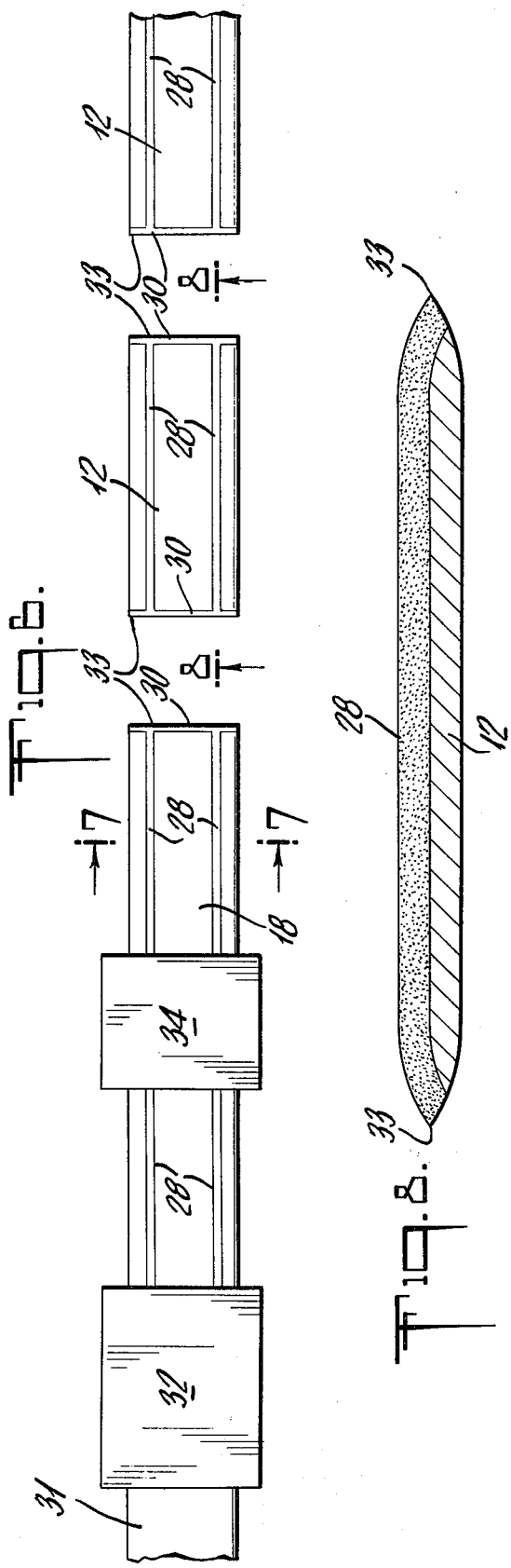
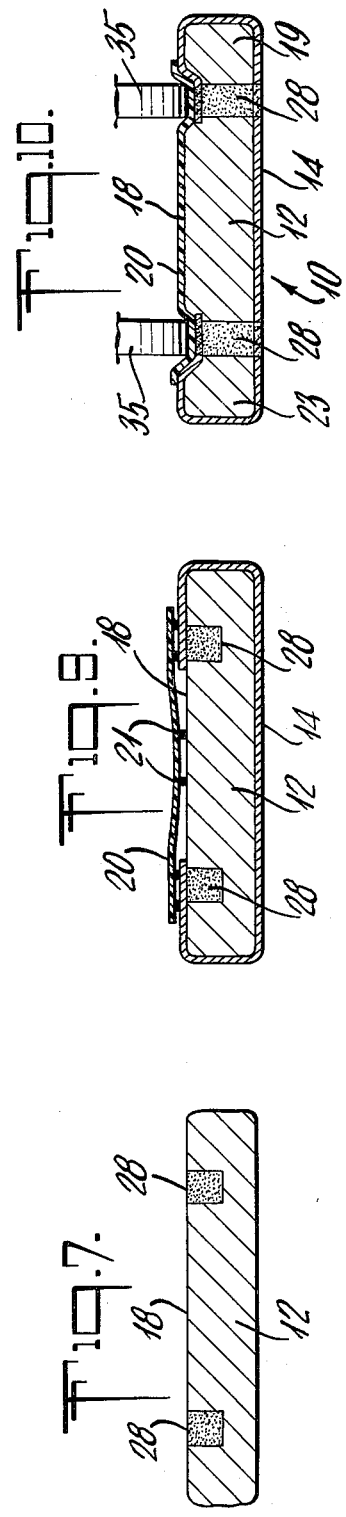

ABSORBENT PRODUCT WITH SIDE LEAKAGE CONTROL MEANS

BACKGROUND OF THE INVENTION

This invention relates to absorbent products and, more particularly, relates to products used for absorbing and retaining body fluids and worn in contact with the body such as diapers, sanitary napkins, dressings and the like.

In general, such products comprise one or more layers of a core of hydrophilic material such as wood pulp, rayon, gauze, tissue or the like and in some cases, synthetic hydrophilic material such as hydrophilic polyurethane foam. The hydrophilic material is generally provided in the form of a pad usually having a rectangular shape and enveloped in a cover which can be a woven gauze or a nonwoven fabric material that is pervious to body fluids on at least the side of the pad designated to be placed against the body. The cover on the side of the pad facing away from the body often is impervious to body fluids in an effort to protect the clothing from staining and wetting.

The absorbent product is positioned on the body so that the body fluid being absorbed strikes the pad in a central area thereof and, ideally, should then be evenly distributed by wicking action throughout the entire pad. The ideal situation of even distribution will make maximum use of the absorbent material in the product and thus, in theory, the outer surfaces will not be wet and the pad will not need to be changed until all of the absorbent material is saturated.

Unfortunately, the real situation is far from this ideal. In practice, fluid striking a major surface of a rectangular pad is first absorbed into the pad for a certain distance and then wicks radially in all directions. Since the width of the rectangular pad is less than its length, fluid wicking radially first wets an outer surface at the longitudinally extending side edges of the pad. While this occurs long before the entire pad is totally saturated, since the edges of the pad are wet, it is necessary to change the pad even though only a small portion of the potential absorption capacity has been utilized.

The art, therefore, has directed its efforts to solving this side leakage problem. One solution, employed with such products such as diapers and sanitary napkins, is to provide an impervious cover sheet on the side of the pad facing away from the body, this sheet being sized wider than the pad, i.e., extending beyond the pad along each longitudinal edge. The wide edges are then folded to cover the longitudinally extending side edges of the pad and preclude the passage of fluid therethrough. Unfortunately, this construction imparts undesirable side effects when the impervious cover sheet, normally a polymeric film, is placed against or in juxtaposition with the skin of the user for a period of time. This is due to the inherent nature of most commercially used substances for the impervious sheet, e.g., polyethylene, which have extremely poor moisture vapor and gas transmission properties so that in the areas where they contact the skin, they substantially inhibit moisture vapor and gas transmission, thereby retaining moisture vapor in contact with the skin and leading to irritation and the formation of rashes, etc.

It has also been proposed in the prior art that the edges of the absorbent liquid product be coated with a liquid impermeable material such as wax whereby the edges are effectively sealed against absorption. This situation is substantially the same as the use of a polymeric film described above and suffers from the same drawback, to wit: that the waxed edge fails to transmit vapor and gas and hence, leads to skin irritation when worn for a length of time. A similar attempt to solve the side leakage problem is described in U.S. Pat. No. 3,559,649 where a fluid repellent material is applied to the edges of a covered pad of absorbent material. Once again, the problem of skin irritation is encountered.

Significant progress in this area was made by the invention disclosed in Canadian Patent 884,608 issued to Yvon G. Levesque on Nov. 2, 1971. Described therein is an absorbent product and a method for making the same wherein a zone extending from the outer edge of each longitudinal side of an absorbent pad is treated so as to be hydrophobic and yet is still porous and hence, capable of moisture vapor and gas permeability. While this permeability has greatly reduced the tendency for skin irritation, the problem still exists, particularly in such products as sanitary napkins and diapers where the skin in contact with the edges of the product is apt to be moist. Moreover, another problem has been discovered when attempting to manufacture the product disclosed by this Canadian Patent under high speed production conditions. As disclosed, the extreme side margins of the pads are rendered hydrophobic by applying thereto a liquid repellent composition and then compressing the thus treated margins to distribute this composition throughout the zone and throughout the longitudinal sides of the pad. The composition eventually dries leaving this margin hydrophobic. Unfortunately, the drying process does not occur immediately with the disadvantageous result that to maintain a high rate of production a plurality of products must be stacked and packaged while still in the wet state, the sides of the so-packaged products contact the walls of the packaging material and are capable of adhering thereto so that when removed, frequently the packaging material fails and leaves a residue on the product and/or the cover material on the product fails and remains adhered to the package. In view of these shortcomings, a still more satisfactory solution to the problem of side leakage has been sought.

SUMMARY OF THE INVENTION

It has now been discovered that an absorbent product can be provided which solves the problem of side leakage without introducing the concommitant problem of skin irritation and can still be manufactured at high production rates. Specifically, there has been provided an improvement in an absorbent product for absorbing and retaining body fluids of the kind comprising an absorbent element of porous hydrophilic material as the absorbent medium, the absorbent element having first and second major surfaces and side and end edges. The improvement comprises providing means for retarding premature failure of the product by leakage of body fluids from the side edges while still maintaining the side edges soft and absorbent. More specifically, such means comprise providing, in a narrow zone of the absorbent element extending along each of the side edges but spaced away from each side edge, an impregnation of hydrophobic material which is distributed throughout the zone, from major surface to major surface, while leaving the extreme marginal portion between the impregnated zone and the side edge free of such impregnation.

Several distinct advantages accrue from the above described construction. Firstly, the primary object of precluding side leakage is accomplished in that body fluid striking the center of the absorbent element will wick in a direction radially from such central contact only so far, in a transverse direction to the element, as the impregnated zone. At that point, wicking will then proceed longitudinally, thus utilizing far more of the absorbent material in the product then would be utilized in the absence of such a hydrophobic zone.

In accordance with this instant invention, however, the extreme marginal portions of the absorbent element are free of hydrophobic impregnant and hence, retain their hydrophilic properties and the natural softness of the element. Accordingly, the sides of the product which make contact with the body are free to absorb body moisture, thus entirely eliminating the skin irritation heretofore associated with products of this kind.

Still another advantage occurs by applying the teachings of this invention. In view of the fact that the hydrophobic zone is displaced inwardly from the extreme side of the absorbent element, the hydrophobic zone may be applied by impregnating that portion of the element with a wet solution and still manufacture the product at high production rates. Inasmuch as the edges are free of impregnate and hence, at all times dry, the product may be packaged while still in the wet state without the heretofore encountered risk of adhering the product to the walls of the packaging material.

In a specific embodiment of the invention, the absorbent element may be incorporated into a sanitary napkin. In this instance a cover is provided overlying the major surfaces, the cover being pervious to body fluids on at least one major surface, i.e., the surface to be worn against the body. The second major surface may be covered with the same pervious cover or instead (or in addition thereto) may be provided with a body fluid impervious cover to prevent staining of the users underclothing.

In another specific embodiment, the absorbent element may be incorporated into a disposable diaper. In this case, the element is enveloped by a body fluid impervious facing sheet, which overlies the first major surface and a body fluid impervious backing sheet, overlying the second major surface.

In accordance with this invention, a method is also provided for producing the absorbent products described herein wherein a fluid hydrophobic material is applied to one surface of the absorbent element in a narrow longitudinally extending zone extending along each of the side edges but spaced away from each side edge. Subsequent to such application, the zone is subjected to a compressing step whereby the hydrophobic material impregnates throughout the zone from major surface to major surface.

BRIEF DESCRIPTION OF THE DRAWINGS

The invention is illustrated in the appended drawings wherein:

FIG. 1 is a perspective view of a sanitary napkin embodying this instant invention and shown with the major surface to be worn against the body facing upwardly and with parts removed to show internal structure;

FIG. 2 is a perspective view of the sanitary napkin of FIG. 1 with the surface to be worn against the body facing downwardly and with parts removed to show internal structure;

FIG. 3 is an enlarged cross-sectional view of the napkin shown in FIG. 1 and taken through line 3—3;

FIG. 4 is a schematic, planar view of a sanitary napkin embodying the invention and illustrating the initial pattern of fluid spreading;

FIG. 5 is a schematic, planar view of the sanitary napkin of FIG. 4, illustrating the pattern of fluid spreading at a later time;

FIG. 6 is a planar schematic view of a part of a sanitary napkin line illustrating steps in a method for producing napkins embodying the invention;

FIG. 7 is a transverse cross-sectional view of the line illustrated in FIG. 6 and taken along line 7—7;

FIG. 8 is a longitudinal cross-sectional view of the line illustrated in FIG. 6 and taken along line 8—8;

FIG. 9 is a transverse cross-sectional view of a partially completed sanitary napkin at a point in time in its manufacture later than that of FIGS. 6–8; and FIG. 10 is a transverse cross-sectional view of an essentially completed sanitary napkin at a point in time in its manufacture later than that of FIG. 9.

DETAILED DESCRIPTION OF THE INVENTION

Referring now to FIGS. 1–3 of the drawings, illustrated therein in perspective and cross-sectional views is a sanitary napkin 10 embodying the teachings of this invention. The napkin consists of an absorbent element 12 which is shown in the form of a generally rectangular pad and may consist of loosely associated absorbent hydrophilic material such as cellulosic fibers, e.g., wood pulp, regenerated cellulose or cotton fibers; other chemically or physically modified cellulose fibers; other polymeric absorbent materials, both natural and synthetic, such as hydrophilic foams (e.g. hydrophilic polyurethane foam); or may be such commonly used absorbent material as wadded tissue paper or the like. Alternatively, the absorbent element 12 may be a shaped form such as molded hydrophilic polymer (e.g. a molded hydrophilic polyurethane foam or a molded cellulosic foam) or any combination of these absorbent materials.

A fluid pervious cover 14 envelops the first major surface 15, which surface is designed to contact the body; the longitudinal sides 16 and 17; and the extreme longitudinal marginal portions of the second major portion 18, designed to be worn away from the body. The cover 14 may be any woven or nonwoven material pervious to body fluid striking its surface, such covers being well known in the art. Overlying the second major surface 18 is a fluid impervious layer 20 provided to preclude fluid from passing onto an undergarment and which may be any thin flexible impervious layer, for example, a polymeric film such as polyethylene or polypropylene, cellophane or a usually fluid pervious material that has been treated to be impervious such as impregnated fluid repellant paper.

Adhesive 21 is applied to that surface of the impervious layer 20 which faces the absorbent element 12 and will permeate through the portions of the pervious cover 14 overlying the second major surface 18, securing both the impervious layer 20 and the pervious cover 14 to the absorbent element 12. Likewise, the ends 22 of the product may be secured by adhering the pervious cover and the impervious layer together where they extend beyond the ends of the absorbent element 12.

The product may be applied to the body by any of the means well known in the art such as, for example, with pins, belts or the like. As shown in the drawing, attachment means are provided which comprise a strip of pressure sensitive adhesive 24 being applied to a central portion of the second major surface for adhering the product in place on an undergarment. A protective cover 26 is provided to overlie the adhesive strip 24 which may be peelably removed just prior to use.

In accordance with the teachings of this invention, a narrow zone 28 extending along each of the side edges of the product is provided impregnated with a hydrophobic material, the impregnation being distributed throughout the zones 28 from the first major surface 15 to the second major surface 18. Further, the extreme marginal portions 19 and 23 extending along the longitudinal edges of the product are maintained free of the impregnation and hence are soft and absorbent. In the preferred embodiment of this invention, further zones 30 are provided extending along the transverse ends of the absorbent element 12 and preferably from the first through the second major surfaces. Because these ends do not normally make the same intimate contact with the body, it is not necessary that the extreme marginal ends of the absorbent element be free of impregnate.

The impregnate may comprise any medically acceptable hydrophobic material of a permanent, preferably non-volatile and desirably non-migrating nature. Typical examples of such materials are the thermosetting, waxy resins sold by the Ciba Company, under the trademark "Phobotex FTA"; the emulsions of wax and aluminum salts sold by American Cyanamid Co. under the trademark "Paramul"; the Fluorochemical type of compositions sold by the 3M Corporation under the trademark "Scotchgard"; the silicone emulsions sold by the Dow-Corning Corporation as "Dow-Corning 108"; the chrominum complex compositions such as those sold by E. I. du Pont de Nemours & Co. under the trademark "Quilan Chrome Complex" and by the U.S.M. Corporation under the trademark "Kromyil-s"; other water-repellant compositions sold by E. I du Pont de Nemours & Company and American Cyanamid Co. under the trademarks "Aridex" and "Aerotex", respectively; and the long chain nitrogen complex based compositions sold by E. I. du Pont de Nemours & Co. under the trademark "Zelan". The materials of choice are the silicone emulsions and the chromium complex compositions.

The amount of hydrophobic material with which the treated zone is impregnated will vary depending on such factors as the kind of absorbent material being treated and the kind of hydrophobic material employed. Generally speaking, no more impregnant should be used than is necessary to provide an effective barrier to side leakage. Based on the weight of dry absorbent material in the treated zone, the weight of hydrophobic material can comprise as little as 0.25% thereof and up to about 120% or more.

A range from about 0.50 to about 5% has been found to be satisfactory with the employment of the most commonly used absorbent materials.

The advantages of this invention can be best illustrated by reference to FIGS. 4 and 5 which schematically illustrate an absorbent product embodying these teachings shown in planar view with the body contacting major surface 15 facing upwardly. As contemplated, the product has been applied to the body so that the body fluid to be absorbed strikes the product in approximately the center, designated in the drawings by the letter X. Upon the continued deposition of body fluid and by the wicking action of the absorbent material comprising the absorbent element 12, the body fluid being deposited begins to spread radially from the point of contact. As is illustrated in FIG. 4, the pattern of spread 29 approaches the longitudinal edges 17 and 16 long before it nears the transverse ends 22. Absent any of the treatment prescribed herein, this pattern of spread would soon wet the longitudinal edges and hence, require changing the product even though only a small portion of the absorbent element 12 is actually utilized. However, in accordance with the teachings of this invention, zones 28 have been provided impregnated with hydrophobic material. Accordingly, as is illustrated in FIG. 5, the fluid pattern 29', once it has approached the zones 28, ceases to extend closer to the longitudinal edges and instead, expands toward the transverse ends 22, thus making efficient utilization of the absorbent capacity of the element 12.

As can be seen schematically in FIGS. 4 and 5, the extreme marginal portions 19 and 23 extending along the longitudinal edges of the product are both free of impregnant and likewise free of body fluid derived from that fluid striking the center of the napkin. Accordingly, these edges are soft and absorbent and, in the case of a sanitary napkin, for example, will advantageously absorb moisture, e.g., perspiration from the skin of the user. These properties of softness and absorbency are believed to be the reason that, unlike prior attempts to control edge leakage, products embodying the teachings herein do not concomitantly cause skin irritation.

The hydrophobic zones should be of a width great enough to provide a barrier for body fluid, but no so great as to effect the absorbent properties of the product as a whole. Preferably, such width may range from about 0.05 to about 0.5 inches and more preferably, from about 0.1 to about 0.25 inches. The impregnant free extreme margins 19 and 23 should be of a width great enough to provide a comfortable interface between the hydrophobic zones and the body when the product is worn, but again should not be so wide as to substantially detract from the body fluid absorbent capacity of the product as a whole. Preferably, these extreme margins may range from about 0.075 to about 0.75 inches wider and more preferably, from about 0.1 to about 0.5 inches.

FIGS. 6 through 10 schematically illustrate a preferred method for manufacturing the product described and illustrated in FIGS. 1-3. In FIG. 6 is shown a schematic planar view of a manufacturing line. An elongated web or snake of loosely associated absorbent material 31, e.g., wood pulp fluff, is supported on a moving belt (not shown) and carried thereby under a hydrophobic material application station 32 whereby two continuous zones 28 of hydrophobic material are deposited onto the upwardly facing surface of the web. The hydrophobic material application station may comprise metering valves, jet nozzles or any other means known in the art for depositing lines of fluid onto a moving web. As can be best seen in FIG. 7, which is a transverse cross sectional view of the web after it leaves the station 32, the hydrophobic material is limited to discrete zones 28 and penetrates only partially from surface 18 into the thickness of the web 31.

The next web passes under cutting station 34 whereby means known in the art, such as for example, a rotating cutting knife, the moving web is cut at spaced intervals to form a plurality of rectangular absorbent elements 12. The cutting action compresses the loosely associated absorbent material in the ends 33 of the cut absorbent elements thereby decreasing the capillary spaces therebetween and hence, increasing the ability of the ends to wick fluids. This, in combination with the pressure exerted by the cutting knife, drives the deposited hydrophobic material through the full thickness of the element and transversely across the ends. In this manner, the preferred transverse zones 30 having an impregnation of hydrophobic material are provided on the product without any additional processing steps. The cut element 12 is illustrated in longitudinal cross-section in FIG. 8. As can be seen from this FIG. 8, at the end portions, hydrophobic zones 30 extend throughout the thickness of the element while the longitudinal hydrophobic zones 28 still extend only partially through the element thickness.

After cutting, the element then undergoes further manufacturing steps whereby the fluid pervious cover 14 and the fluid impervious layer 20 as described in connection with FIGS. 1-3, are applied and adhered together by means of adhesive 21. The method for performing these manufacturing steps are all known to those skilled in the art. FIG. 9 illustrates, in transverse cross section, the product 10 at the completion of these steps. It should be noted that the hydrophobic zones 28 still extend only partially into the thickness of the absorbent element 12.

FIG. 10 illustrates the preferred method whereby the hydrophobic zones 28 are finally extended throughout the thickness of the absorbent element 12. The product 10, again shown in transverse cross-section and again on a conveyor such as an endless belt, is now passed under and compressed by two metal compression rollers 35 which are of a width such that pressure is exerted solely on an area co-extensive with the hydrophobic zones 28. In a manner similar to that resulting from the above described cutting step, the effect of such compression is to decrease the capillary spaces between the absorbent material in the compressed zones and thereby increase the ability of these compressed zones to wick fluid. This, in combination with the pressure exerted by the compression rollers 35, drives the hydrophobic material through the full thickness of the pad. At the same time, because of the selection of compression rollers of a width essentially the same as that of the zones 28, the hydrophobic material is limited to these zones and, in accordance with the teachings herein, the extreme marginal portions 19 and 23 are free of such hydrophobic material.

The drawings and the description thereof relate to one specific embodiment of this invention, namely an adhesively attached sanitary napkin having a body fluid pervious cover on one side, a body fluid impervious layer on the other and an absorbent element therebetween with pressure sensitive adhesive being employed as means for attaching the product during use. It will be understood, however, that this embodiment is merely illustrative of the teachings herein and that the teachings apply with substantial advantage to other similar products. For example, the invention may apply to sanitary napkins of the type well known in the art which comprise an absorbent element completely wrapped in a fluid pervious cover or such a product wherein a fluid impervious layer is incorporated within or immediately adjacent to the surface of the absorbent element. Further, the teaching herein applies to sanitary napkins wherein means other than pressure sensitive adhesive is employed as attachment means, tabs, belts, and the like being illustrative of these latter types. Still further, the invention is applicable to other kinds of absorbent products now in use and to be worn against the body with diapers and surgical dressings being examples thereof.

The advantages of the instant invention can be better understood by reference to the following Example.

EXAMPLE

A first series of sanitary napkins were prepared having the configuration of those shown in FIGS. 1-3. The napkins had overall rectangular dimensions of 7.5 inch by 2.0 and were 0.38 inch thick. The absorbent element was a rectangular pad of comminuted wood pulp having the overall dimensions of 6.38 inch by 2.0 inch by 0.38 inch and wrapped in a body fluid pervious nonwoven cover comprising rayon fibers bound together with an adhesive acrylate binder. The impervious layer is a sheet of polyethylene film having a thickness of about 2 mils.

The absorbent element, the impervious layer and the pervious layer of these napkins are identical in all respects to the sanitary napkin made by Personal Products of Milltown, New Jersey and sold by them as STAYFREE mini-pads.

In accordance with the teachings of this invention, a 2% by weight solution of the aforementioned Kromyl-s is used to impregnate two longitudinally extending zones such as those shown in FIGS. 1-3. Because the method of impregnation is that described above, two transverse zones, at each end of the absorbent element are likewise impregnated. The longitudinal zones are each about 0.162 inch wide and the outer longitudinal edge of each zone is about 0.25 inch from the nearest outer longitudinal edge of the rectangular pad. Approximately 0.44 gms of the 2% Kromyl-s solution is deposited on each pad and the pads are allowed to dry leaving a residual add on, based on the weight of wood pulp in the treated zone of 1.9%.

A second series of sanitary napkins are prepared, identical in every respect to the first series with the exception that no hydrophobic treatment is applied to the absorbent element. Both series of napkins are tested in a Dynamic Form test in which a napkin is adhered to a rubber mold which simulates the female form. The napkin is held in place using commercially available panty hose. The form is set into motion by means of a set of gears, cams and rods to simulate a walking motion and an ersatz menstrual fluid containing one percent NaCl, by weight, is allowed to drip onto the napkin. The fluid is applied at a rate of 3.4 cc. per minute and the form is operated at a speed of 60 cycles per minute. The end point of the test is determined by noting when fluid spills over any edge of the product, at which point, the total quantity of fluid absorbed by the napkin is recorded as the napkin capacity.

Table I summaries the results obtained by testing the two series of napkins:

TABLE I

| Samples | Avg. Weight* (gm.) | Avg. Capacity (cc.) | Avg. Capacity/ Weight (cc/gm) |
|---|---|---|---|
| Treated Napkins | 3.83 | 17.8 | 4.65 |
| Untreated Napkins | 3.76 | 5.5 | 1.46 |

*Based on total napkin weight, dry

In each case described above, the napkin failure occured because of side leakage. As the data clearly shows, a more than three fold improvement in the capacity of the napkin was realized by incorporating the teachings of this invention.

In addition to the above, a controlled panel used the napkins of this invention and the above improvement was manifested under actual use conditions.

What is claimed is:

1. An absorbent product for absorbing and retaining body fluids and comprising an absorbent element of porous hydrophilic material as the absorbent medium, said absorbent element having first and second major surfaces and longitudinal side edges and transverse end edges therebetween; the improvement wherein means are provided for retarding premature failure of said product by leakage of said body fluids from said side edges while still maintaining said side edges soft and absorbent, said means comprising a narrow, longitudinally extending zone extending along each of said side edges but spaced away from each of said side edges, said longitudinally extending zone being impregnated with a hydrophobic material from major surface to major surface, the extreme marginal portions of said absorbent element along said longitudinal edges being free of said impregnation.

2. The absorbent product of claim 1 wherein a transverse zone extending along each of said transverse end edges is provided, said transverse zone being impregnated with a hydrophobic material from major surface to major surface.

3. The absorbent product of claim 1 wherein said longitudinally extending zone ranges from about 0.05 to about 0.5 inches wide.

4. The absorbent product of claim 3 wherein said longitudinally extending zone is from about 0.1 to about 0.25 inches wide.

5. The absorbent product of claim 1 wherein said extreme marginal portion is from about 0.075 to about 0.75 inches wide.

6. The absorbent product of claim 5 wherein said extreme marginal portion is from about 0.1 to about 0.5 inches wide.

7. The absorbent product of claim 1 wherein the quantity of hydrophobic material in said longitudinally extending zone is from about 0.25 to about 120% by weight, based on the hydrophobic material-free weight of said longitudinally extending zone.

8. The absorbent product of claim 1 wherein the quantity of hydrophobic material in said longitudinally extending zone is from about 0.50 to about 5% by weight, based on the hydrophobic material-free weight of said longitudinally extending zone.

9. The absorbent product of claim 1 as a sanitary napkin, said absorbent element having a cover overlying said first and second major surfaces, said cover being porous to body fluid on at least said first major surface.

10. The sanitary napkin of claim 9 wherein said cover is body fluid impervious on said second major surface.

11. The sanitary napkin of claim 10 wherein said cover comprises a body fluid pervious cover overlying the first major surface, the longitudinal side edges and the extreme longitudinal marginal portions of said second major surface.

12. The absorbent product of claim 1 as a disposable diaper wherein said absorbent element is enveloped by a body fluid pervious facing sheet overlying said first major surface and a body fluid impervious backing sheet overlying said second major surface.

* * * * *